US008759758B2

(12) United States Patent
Steiner et al.

(10) Patent No.: US 8,759,758 B2
(45) Date of Patent: Jun. 24, 2014

(54) GAS CHROMATOGRAPH-MASS SPECTROMETER TRANSFER LINE

(75) Inventors: Urs Steiner, Branford, CT (US); Felician Muntean, Danville, CA (US); Bert D. Egley, Walnut Creek, CA (US)

(73) Assignee: Bruker Daltonics, Inc., Billerica, MA (US)

( * ) Notice: Subject to any disclaimer, the term of this patent is extended or adjusted under 35 U.S.C. 154(b) by 0 days.

(21) Appl. No.: 13/418,743

(22) Filed: Mar. 13, 2012

(65) Prior Publication Data

US 2013/0256523 A1 Oct. 3, 2013

Related U.S. Application Data

(60) Provisional application No. 61/508,304, filed on Jul. 15, 2011.

(51) Int. Cl.
*H01J 49/04* (2006.01)
*G01N 30/72* (2006.01)
(52) U.S. Cl.
CPC ............. *H01J 49/0422* (2013.01); *H01J 49/04* (2013.01); *G01N 30/7206* (2013.01)
USPC ........................................................ 250/288
(58) Field of Classification Search
CPC .................................................. G01N 30/7206
USPC ........................................................ 250/288
See application file for complete search history.

(56) References Cited

U.S. PATENT DOCUMENTS

| | | | | |
|---|---|---|---|---|
| 2,531,065 A | * | 11/1950 | Livingood et al. | 313/62 |
| 4,213,326 A | * | 7/1980 | Brodasky | 73/23.37 |
| 4,388,531 A | * | 6/1983 | Stafford et al. | 250/427 |
| 4,641,541 A | * | 2/1987 | Sharp | 73/864.81 |
| 4,804,839 A | | 2/1989 | Broadbent et al. | |
| 4,985,625 A | * | 1/1991 | Hurst | 250/288 |
| 5,196,700 A | | 3/1993 | Kameshima | |

(Continued)

FOREIGN PATENT DOCUMENTS

JP 63225707 A * 9/1988

OTHER PUBLICATIONS

7200 GC/Q-TOF Breakfast Seminar, ASMS Conference on Mass Spectrometry and Allied Topics, Jun. 5-9, 2011 Colorado Convention Center, Denver, CO, p. 12.

(Continued)

*Primary Examiner* — Jack Berman
*Assistant Examiner* — James Choi
(74) *Attorney, Agent, or Firm* — Robic, LLP

(57) ABSTRACT

A transfer line for conveying the column effluent from a gas chromatograph to an ion source of a mass spectrometer has a transfer line body and a mechanism for moving the transfer line body either towards or away from the mass spectrometer. A gas seal between the housing of the mass spectrometer and the transfer line body prevents vacuum leak when the transfer line body is moved. In one embodiment, the transfer line body outer periphery is threaded and a hand wheel engages the transfer line body threads via complementary threads in order to move the body. When the transfer line is moved towards the mass spectrometer, the body presses an ion source, which is not rigidly fixed to the housing of the mass spectrometer, into a recess seat of the housing, and aligns the ion source in an operating position.

14 Claims, 2 Drawing Sheets

(56) References Cited

U.S. PATENT DOCUMENTS

| | | | |
|---|---|---|---|
| 5,281,397 A * | 1/1994 | Ligon et al. | 422/89 |
| 5,644,130 A | 7/1997 | Raatz | |
| 6,006,584 A * | 12/1999 | Itoi | 73/23.37 |
| 7,709,790 B2 * | 5/2010 | Guckenberger et al. | 250/288 |
| 2006/0163471 A1 * | 7/2006 | Zapata et al. | 250/288 |
| 2007/0007448 A1 * | 1/2007 | Wang | 250/288 |
| 2011/0174969 A1 | 7/2011 | Seyfarth | |
| 2011/0174970 A1 * | 7/2011 | Chalker et al. | 250/288 |
| 2012/0097844 A1 * | 4/2012 | Newton | 250/288 |
| 2012/0223522 A1 * | 9/2012 | Graham | 285/385 |

OTHER PUBLICATIONS

Agilent 7890 GC/6540 QTOF LC/MS System with GC-APCI Interface Technical Overview, Published in the U.S.A. Mar. 3, 2011, p. 3.

* cited by examiner

GAS CHROMATOGRAPH-MASS SPECTROMETER TRANSFER LINE

BACKGROUND

The invention relates to a heated gas sample transfer line from a gas chromatograph (GC) to an ion source of a mass spectrometer (MS). Various combinations for coupling of gas chromatographs (GC) with mass spectrometers (MS) are known in the art. In the GC, samples are injected onto a GC column through an injection port and become separated while passing through the GC column. The effluent of the GC column is conveyed from the GC oven to the ion source of the MS within a column extension of a transfer line. In the ion source, the sample molecules are ionized, for example by electron impact or chemical ionization, before being analyzed according to their mass-to-charge ratios.

During the transfer of the effluent from the GC column oven to the ion source, it is necessary to maintain a uniform temperature along the column extension. If a significant temperature gradient exists so that the temperature varies at different points along the column extension, cold spots may occur to cause condensation from the gas phase of the sample so that it will either not be passed through to the MS or will exhibit excessive chromatographic peak broadening or peak tailing. On the other hand, hot spots that appear may cause some compounds to degrade thermally with a resultant change in their chemical structure. Similar effects can occur even if the transfer line is at uniform temperature if the temperature of the transfer line is either too cold or too hot during the elution of any given chemical compound. Additionally, excessive temperatures of transfer line can lead to elevated "chemical noise" and lower signal-to-noise ratio for any given analytical results. Temperature variations along the length of the transfer line of +/−10° Celsius are generally acceptable, although variations of less than +/−5° Celsius are required in some applications.

Usually, GC-MS transfer lines are rigidly attached to the housing of the mass spectrometer and provide a uniform temperature environment on the column extension when column effluents are conveyed through the walls of the GC oven and the mass spectrometer into the ion source.

MS ion sources have to be cleaned in regular periods, or the filaments for electron generation have to be replaced. For these maintenance operations, the ion sources have to be taken out of the MS housing. Generally, they are mounted with fasteners that are sometimes hard to access, require clean tools and potentially can be lost inside the instrument. In addition, the column extension has to be removed from the transfer line, and the transfer line has to be disconnected from the ion source, always with a risk to damage the GC column or the column extension, respectively.

SUMMARY

In a first aspect, the invention provides a transfer line for conveying the column effluent of a gas chromatograph to an ion source of a mass spectrometer, comprising: a transfer line body, means for moving the transfer line body, and gas seal between the housing of the mass spectrometer and the transfer line body to prevent a vacuum leak when the transfer line body is moved by the means. The means can move the transfer line body along its axis between two end positions (extended/retracted end position). Inside the transfer line body, the column effluents are conveyed within an extension of the gas chromatography column (column extension) into the ionization chamber of the ion source, where the sample molecules are ionized, for instance, by electron ionization (EI) or by chemical ionization (CI).

In a first embodiment, the gas seal comprises bellows fastened to the transfer line body and to the housing of the mass spectrometer such that the transfer line body is movable between two end positions without breaking the vacuum in the mass spectrometer. The bellows can be structured to exert a force on the transfer line body, preferably directed towards the inside of the mass spectrometer. Preferably, the transfer line body comprises threads and the means for moving comprises a hand wheel engaging the transfer line body via complementing threads. On the other hand, the means for moving can also comprise a pump for evacuating the ion source region and generating a force on the transfer line body which extends from outside the mass spectrometer into the evacuated ion source region. Thus, the transfer line body is move by the forces on the bellows generated by the evacuation and venting processes due to the changing pressure differences.

In a second embodiment, the gas seal comprises at least one sealing ring (O-ring) positioned between the transfer line body and the housing of the mass spectrometer. Here, the transfer line body preferably comprises threads and the means for moving comprises a hand wheel engaging the transfer line body via complementing threads.

In a third embodiment, the transfer line body comprises a head piece that forms a part of the ion source, when the transfer line is in the extended end position. The column effluents are conveyed in the column extension and released at a head piece into the ionization chamber of the ion source. The head piece can comprise an electrically insulated electrode serving as an ion repelling electrode in the ion source, when an appropriate voltage is applied to the electrode.

In a fourth embodiment, the transfer line body comprises an inner tube that contains an extension of the column of the gas chromatograph and that is fastened to the column of the gas chromatograph, inside the oven, in a vacuum-tight manner by a ferrule and compression nut. Furthermore, the transfer line can comprise a gas inlet between gas chromatograph and mass spectrometer to convey additional gas to the ion source, for example to provide the ion source with an appropriate gas for chemical ionization. The additional gas is preferably conveyed to the ion source in the tubular space between the inner tube and the column extension. The transfer line can further comprise a heating cartridge and a temperature sensor to heat the inner tube and the column extension inserted in the inner tube to a desired temperature.

In a second aspect of the invention, the transfer line and the ion source are positioned such that the transfer line body presses the ion source, which is not rigidly fixed to the MS housing, into a recess seat of the housing of the mass spectrometer, when the transfer line is moved to the extended end position, and aligns the ion source in an operating position. When the transfer line is retracted and the mass spectrometer (or at least the ion source region) is vented, the ion source is released from being fixed, so that the ion source can be easily removed from the ion source housing, without any further unscrewing or unclamping, only by disconnecting some electrical contacts. The ion source is preferably clamped, but not rigidly attached to the housing of the mass spectrometer after being aligned in the operating position.

Unique to the transfer line according to the invention is that it can simultaneously perform multiple functionalities: providing an isothermal conduit for the GC column effluents, closing the ionization chamber, forming an ion repelling electrode of the ion source, self-aligning and fixing the ion source in place for operation. Venting the ion source region and/or moving the transfer line automatically releases the ion source from the recess seat, allowing easy ion source removal. Upon reinsertion, the ion source is reliably centered and held securely by the force supplied by the transfer line. The bellows, as preferred gas seal, further provide a lower heat-loss from the transfer line to the housing of the mass spectrometer compared to rigidly mounted transfer lines known in the art. The lower heat loss enables a highly homogeneous temperature inside the transfer line and in the column extension, respectively. The intimate thermal contact between the head piece of the transfer line body and the ion source ensure isothermal conditions up to the ion source if the temperature set points for the ion source and the transfer line are equal. The head piece also serves to protect the end of the column extension when removing the ion source for cleaning or during cleaning of the inner walls of the ion source housing without the need to remove the column extension from the transfer line body.

BRIEF DESCRIPTION OF THE DRAWINGS

In FIG. 1, the transfer line is shown in an extended end position after evacuating the ion source region (17). The evacuation generates a pressure difference and causes the bellows (9) to extend. Thereby, the head piece (7) of the transfer line body presses against the ion source (12) and forms one side wall of the ionization chamber (14). The ion source (12) which is not rigidly fastened to the housing (10) is pushed into a recess seat (13) of the MS housing (10) and aligned in an operating position.

In FIG. (2), the transfer line is shown in the retracted end position after venting. The bellows (9) retract the transfer line body and the ion source (12) is thereby released from its recess seat (13). The ion source (12) is free for removal to being cleaned, repaired or replaced. The transfer line body slides through the thermally insulating wall (15) of the GC oven when being moved.

Figure 2:
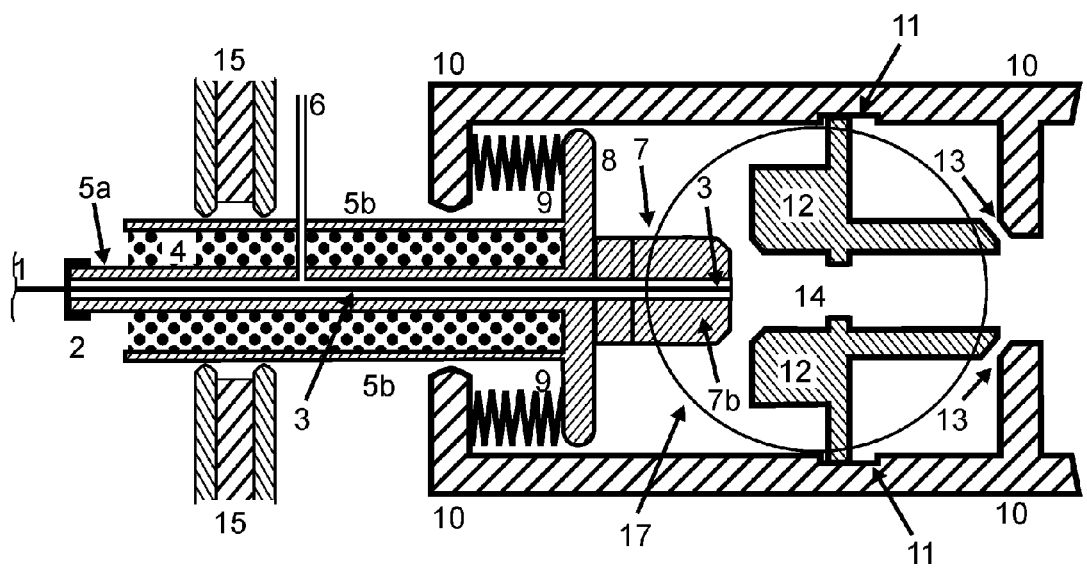
Figure 3:
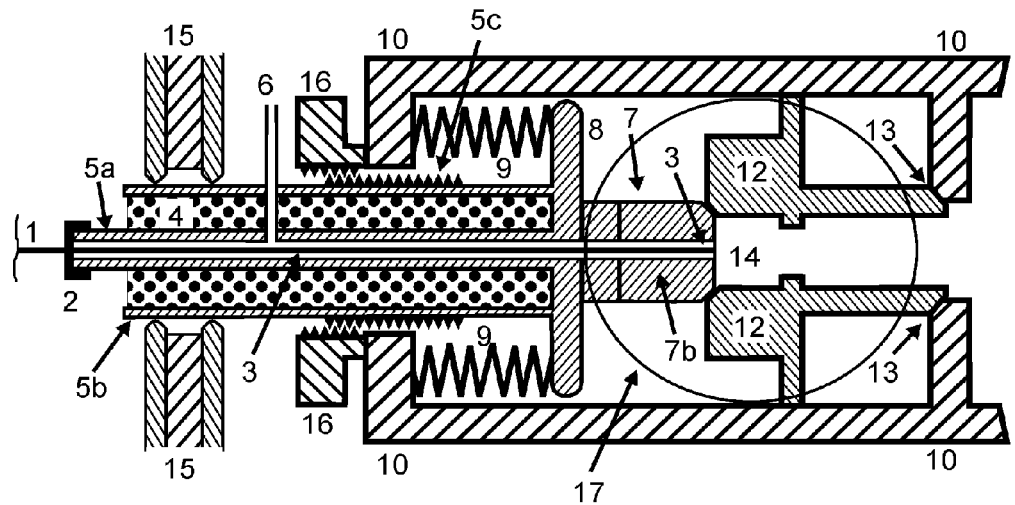

FIG. 3 illustrates a schematic cross-section of a second movable GC-MS transfer line in the extended end position. In contrast to the first embodiment shown in FIGS. 1 and 2, the transfer line body of the second embodiment comprises threads (5a) at outside of the outer tube (5b) and is moved by a hand wheel (16) attached to the housing (10), engaging the transfer line body via complementing threads.

Figure 4:
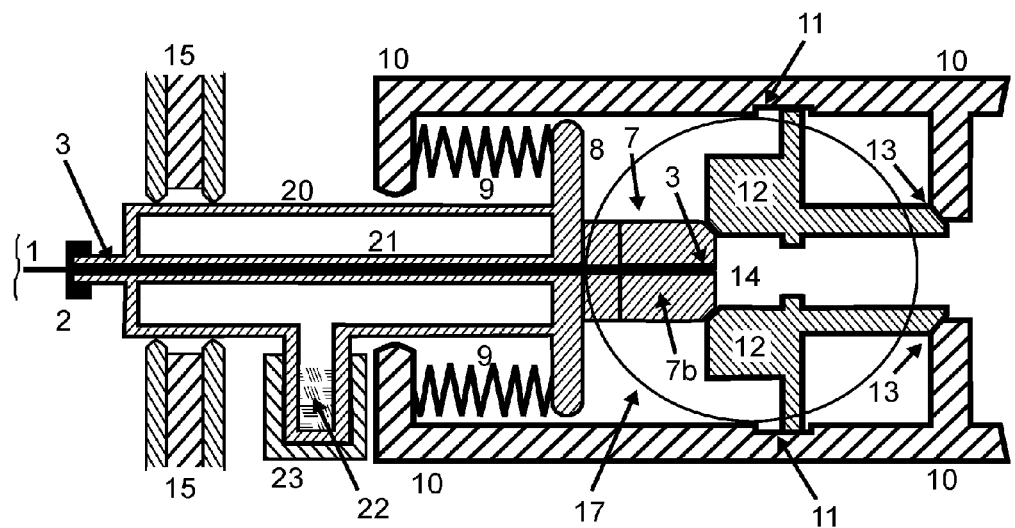

FIG. 4 illustrates schematically a cross-section of a third movable GC-MS transfer line with implementation of a heat pipe. The heat pipe comprises an outer tube (20), an inner tube (21) holding the column extension (3), a fluid reservoir (22), and a heating element (23) with temperature sensor.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

The preferred embodiments will now be described with reference to the drawings. The embodiments shown herein provide movable transfer lines. The transfer lines are located between a gas chromatograph and a mass spectrometer. The details of the gas chromatograph and the mass spectrometer are omitted in the drawings in order to clarify the essential features of the embodiments, only the walls of the GC oven (15) and the housing (10) of the mass spectrometer are shown to some extent. The disclosed transfer lines enable moving a transfer line body along its axis while maintaining the vacuum of the mass spectrometer sealed to the outside atmosphere.

The transfer line body of the preferred embodiments comprises a column extension (3), a head piece (7), a heater cartridge (4), an inner tube (5a), an outer tube (5b), and a plate (8) that connects the column extension (3) and the tubes (5a, 5b). Bellows (9), most preferably metallic bellows, are welded on one side to the plate (8), and on the other side to the housing (10), forming a vacuum-tight connection between the transfer line body and the housing (10), but allowing the transfer line body to move along the axis of the column extension (3) by a few millimeters to some ten millimeters. The GC column (1) is fastened vacuum tight to the inner tube (5a) by a ferrule and compression nut (2) and is extended by extension column (3) up to the head piece (7).

Figure 1:
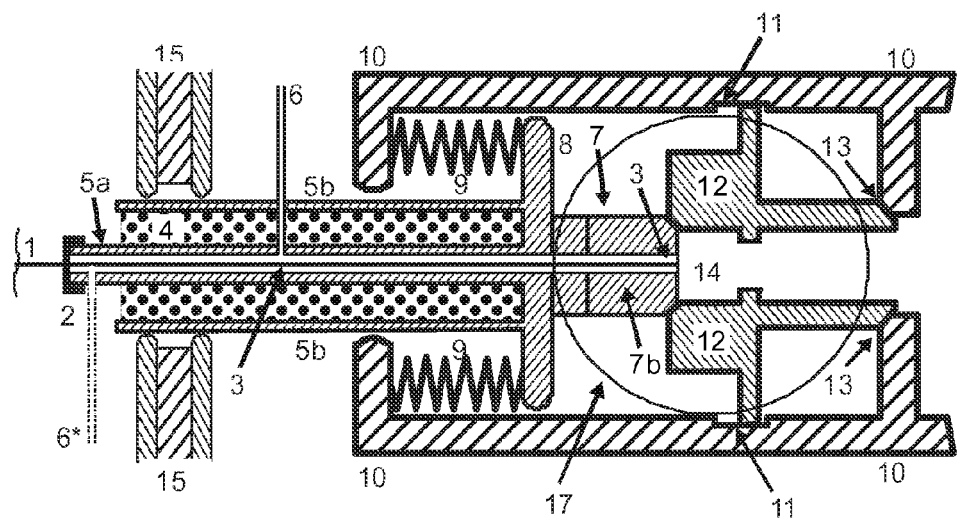
FIGS. 1 and 2 illustrate a schematic cross-section of a first embodiment of a movable GC-MS transfer line according to the present invention.

A first preferred embodiment is illustrated in FIGS. 1 and 2. The transfer line body is presses the against the ion source (12) when the ion source region (17) is evacuated (FIG. 1), and is retracted when the ion source region (17) is vented (FIG. 2). The venting and evacuating of the ion source region (17) generate counteracting forces onto the bellows (9) which can move the transfer line body between the two end positions (extended/retracted end position), shown in FIGS. 1 and 2, when the transfer line body and the bellows (9) are adequately designed.

By moving the transfer line body into the extended position shown in FIG. 1, the transfer line body pushes against the ion source (12) which is not rigidly fastened to the housing (10) such that the ion source (12) is pressed into a recess seat (13) of the housing (10). The ion source (12) is secured in this position by the force supplied by the transfer line body and is aligned by the recess seat (13) in its operating position. The recess (11) in the housing (10) securely guides the ion source (12) between the operating position and the maintenance position, shown in FIG. 2. By venting the ion source region (17), the transfer line is retracted due to the resilient forces of the bellows (9) and the ion source (12) is released for removal. In the maintenance position, the ion source (12) can be easily removed for cleaning, without any unscrewing or unclamping, and without dismounting the transfer line assembly or even disconnecting the GC column. Only the electric contacts have to be disconnected.

In FIG. 1, the ion source region (17) is evacuated and the head piece (7) of the transfer line body forms a side wall of the ion source (12). The head piece (7) comprises an electrode (7b) which is electrically insulated from the transfer line body and the ion source (12). Therefore, the electrode (7b) serves as an ion repelling electrode, when an adequate electric potential is applied to it. A person skilled in the art knows EI and CI ion sources for GC-MS instruments, so it is not necessary to explain these ion sources in detail here. An EI ion source usually comprises: an ionization chamber, elements for heating the walls of the ionization chamber, filaments for electron generation, permanent magnets and yokes to guide accelerated electrons from the filaments into the ionization chamber, ion extraction and acceleration lenses, and contacts for the supply of electric voltages.

The GC column (1) is fastened vacuum tight to the inner tube (5a) by a ferrule and compression nut (2) and is extended by the extension column (3) up to the head piece (7). The transfer line body further comprises a gas inlet (6) between the oven of the gas chromatograph and the mass spectrometer.

The position of the gas inlet (6) is shown by way of example only. It is equally possible to choose another position and/or another orientation along the transfer line body such as indicated with the dashed contour (6*). The additional gas is introduced in the annular space between the column extension (3) and the inner tube (5a). The gas supplied by the gas inlet (6) mixes with the GC column effluent as both enter the ionization chamber (14). The gas may serve as a medium for chemical ionization (CI) of the effluents from the GC column. The transfer line body preferably comprises an electrical cartridge heater (4) inserted into the space between the inner (5a) and the outer tube (5b) to maintain the temperature of the inner tube (5a) and thus of the column extension (3) at a desired value. The temperature is controlled by a feedback loop, which maintains the temperature of a sensor integrated in the electrical cartridge heater (4).

A second preferred embodiment is illustrated in FIG. 3. Equivalent elements of both embodiments share the same reference signs. In this embodiment, bellows (9) are designed to exert a force towards the inside of the mass spectrometer. The bellows (9) push the transfer line body against the ion source (12) and holds it in the extended end position (operating position) even when the ion source region (17) is vented, i.e. the ion source (12) is pre-aligned within the recess seat (13) in the vented state. The pre-alignment prevents a subsequent misalignment of the ion source (12) when the ion source region (17) is evacuated and thus the pressure forces, being exerted on the ion source (12) by the transfer line body, increase. In the vented state, the transfer line body is retracted from the extended end position by a hand wheel (16) which is attached to the housing (10). The exterior of the outer tube (5b) of the transfer line body comprises a thread (5c). A corresponding thread is provided on hand wheel (16). Thus, when the wheel (16) is rotated, it moves the transfer line body in the axial direction up to several ten millimeters, such that the transfer line can be substantially moved between the two end positions. Since the ion source (12) can be held by hand while the hand wheel (16) is turned to move the transfer line body, a recess in the housing (10) is not necessarily required. The bellows (9) maintain the vacuum seal regardless of the position of the hand wheel (16), such that the transfer line can be moved towards the ion source or retracted from the ion source without breaking vacuum.

A third preferred embodiment is illustrated in FIG. 4. Equivalent elements of both embodiments share the same reference signs. In contrast to the first and second embodiment, the transfer line body comprises a well-known heat pipe to maintain the temperature of the inner tube (21) and thus of the column extension (3) at a desired value. The heat pipe consists of the inner tube (21) holding the column extension (3), an outer tube (20), a fluid reservoir (22), and a heating element (23) with temperature sensor. The heating device (23) heats the fluid inside fluid reservoir (22), and the vapor generated condenses at all positions of the inner wall of the heat pipe which are at a lower temperature than the other parts of the heat pipe. The heat pipe holds the temperature along the inner tube (21) highly constant, as a rule much better than +/−1° Celsius. The heat pipe can even be used to heat the ion source (12). A favorable fluid for the heat pipe is water, working well in the temperature region above about 150° Celsius. For lower temperature regimes, a number of other liquids can be used. The simple heat pipe shown in FIG. 4 can be improved by further capillary means along the internal wall, causing the backflow of the fluid to the heater region. The heat pipe can be enclosed by insulating material and an additional tube, so that the outer tube (20) does not contact directly the housing wall (10) or the GC oven wall (15). The transfer line of the third embodiment does not have an additional gas inlet, but a CI line may well be added inside the GC oven at the end of the transfer line.

The above description relates to a specific embodiment of the invention; however, the invention can be implemented using other embodiments to achieve the same improvements and features. It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein.

The present invention has been described in relation to particular examples, which are intended in all respects to be illustrative rather than restrictive. Those skilled in the art will appreciate that many different combinations of hardware, software, and firmware will be suitable for practicing the present invention. Moreover, other implementations of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A transfer line for conveying the column effluent of a gas chromatograph to an ion source having an ionization chamber of a mass spectrometer, comprising:
   a transfer line body comprising a head piece;
   means for moving the transfer line body; and
   a gas seal between a housing of the mass spectrometer and the transfer line body to prevent a vacuum leak when the transfer line body is moved by the means, wherein the transfer line and the ion source are positioned such that the transfer line body presses the ion source, which is not rigidly fixed to the mass spectrometer housing, into a recess seat of the housing of the mass spectrometer in order to align and hold the ion source in an operating position, and wherein the head piece forms a part of the ion source when the transfer line is in an extended end position, thereby closing the ionization chamber.

2. The transfer line according to claim 1, wherein the gas seal comprises bellows fastened to the transfer line body and to the housing of the mass spectrometer such that the transfer line body is movable along its axis between two end positions.

3. The transfer line according to claim 2, wherein the means for moving comprises a pump for evacuating the ion source region and generating a force on the transfer line body.

4. The transfer line according to claim 3, wherein the bellows are structured to exert a force on the transfer line body directed towards the outside of the mass spectrometer.

5. The transfer line according to claim 2, wherein the bellows are structured to exert force on the transfer line body directed towards the inside of the mass spectrometer.

6. The transfer line according to claim 2, wherein transfer line body comprises threads, and wherein the means for moving comprises a hand wheel engaging the transfer line body via complementing threads.

7. The transfer line according to claim 1, wherein the head piece comprises an electrically insulated electrode serving as an ion repelling electrode of the ion source.

8. The transfer line according to claim 1, wherein the transfer line body comprises a heating cartridge and a temperature sensor.

9. The transfer line according to claim 1, wherein the transfer line body comprises a heat pipe.

10. The transfer line according to claim 1, wherein the transfer line body comprises an inner tube that contains an extension of the column of the gas chromatograph and that is fastened to the column of the gas chromatograph, inside a gas chromatograph oven, by a ferrule and compression nut.

11. The transfer line according to claim 10, wherein the transfer line body comprises a gas inlet that is coupled to the inner tube such that gas from the gas inlet is conveyed to the ion source in a tubular space between the column extension and the inner tube.

12. The transfer line according to claim 1, wherein the transfer line body comprises threads, wherein the means for moving comprises a hand wheel engaging the transfer line body via complementing threads, and wherein the gas seal comprises at least one sealing ring positioned between the transfer line body and the housing of the mass spectrometer.

13. A method for aligning an ion source having an ionization chamber to the housing of a mass spectrometer where the ion source is not rigidly fixed to the housing, the mass spectrometer being coupled to a gas chromatograph by a transfer line having a transfer line body, the transfer line body comprising a head piece, means for moving the transfer line body, and a gas seal between a housing of the mass spectrometer and the transfer line body to prevent a vacuum leak when the transfer line body is moved by the means, the method comprising moving the transfer line body to an extended end position so that an end of the transfer line aligns and holds the ion source in an operating position by pressing the ion source into a recess seat of the housing, and in which extended end position the head piece forms a part of the ion source thereby closing the ionization chamber.

14. The method according to claim 13, wherein the ion source is released from the operating position by retracting the transfer line such that the ion source can be removed from the mass spectrometer after venting.

\* \* \* \* \*